United States Patent [19]

Heidlas et al.

[11] Patent Number: 5,714,658
[45] Date of Patent: Feb. 3, 1998

[54] PROCESS FOR THE EXTRACTION OF CAROTENES FROM NATURAL SOURCES

[75] Inventors: Jürgen Heidlas, Trostberg; Georg Huber, Altenmarkt; Jan Cully, Garching; Utz Kohlrausch, Trostberg, all of Germany

[73] Assignee: SKW Trostberg Aktiengesellschaft, Trostberg, Germany

[21] Appl. No.: 701,970

[22] Filed: Aug. 23, 1996

[30] Foreign Application Priority Data

Aug. 25, 1995 [DE] Germany ............ 195 31 254.6

[51] Int. Cl.$^6$ ............ C07C 403/00; C07C 7/10
[52] U.S. Cl. ............ 585/351; 585/240; 585/803; 585/833; 585/864; 585/866
[58] Field of Search ............ 585/240, 351, 585/803, 833, 864, 866

[56] References Cited

U.S. PATENT DOCUMENTS

| | | | |
|---|---|---|---|
| 4,439,629 | 3/1984 | Ruegg | 585/803 |
| 5,019,668 | 5/1991 | Keat et al. | 585/864 |
| 5,246,722 | 9/1993 | Kunst et al. | 426/540 |
| 5,310,554 | 5/1994 | Haigh | 424/439 |
| 5,378,369 | 1/1995 | Rose et al. | 210/637 |

FOREIGN PATENT DOCUMENTS

| | | |
|---|---|---|
| 0278284 | 8/1988 | European Pat. Off. |
| 0455425 | 11/1991 | European Pat. Off. |
| 4342798 | 7/1994 | Germany. |
| 4429506 | 2/1996 | Germany. |

*Primary Examiner*—Glenn Caldarola
*Assistant Examiner*—Bekir L. Yildirim
*Attorney, Agent, or Firm*—Felfe & Lynch

[57] ABSTRACT

For the extraction of carotenes, in particular of β-carotene, from natural sources, these are stirred for several hours at at least 30° C. in a solvent mixture composed of acetic esters of $C_1$–$C_4$ alcohols as well as a portion of 1 to 25% by weight of an oil of biological origin. The natural colorant is in this way obtained in very high space-time yields and high purity.

9 Claims, No Drawings

PROCESS FOR THE EXTRACTION OF CAROTENES FROM NATURAL SOURCES

BACKGROUND OF THE INVENTION

The present invention concerns a process for extracting carotenes which, with the aid of solvent technology, by the selection of suitable solvent mixtures and appropriate process temperatures, enables carotenes, in particular β-carotene, to be extracted from solid, dry or dried natural sources.

Carotinoids are wide-spread in nature and give many natural products such as e.g. carrots, peppers, flowers (French marigolds) or certain microorganisms their characteristic yellow to deep-red color. The carotinoids are divided into two subclasses based on their chemical and structural differences: carotenes which from a chemical point of view are pure hydrocarbons and xanthophylls which contain oxygenated groups (—OH, —O—, =O) in the molecule. Due to the differences in their chemical structure carotenes and xanthophylls, both of which occur as natural accompanying substances of fat, have different solubility properties in organic solvents.

The economic importance of carotene compounds in general and in particular β-carotene has increased steadily in recent times.

On the one hand β-carotene has long been used in food technology as a coloring additive (colorant) or as an antioxidant. The field of application is not restricted to lipid systems but has also been extended to aqueous systems by the use of special technologies such as e.g. diverse encapsulations of β-carotene. On the other hand β-carotene has particular importance in dietetics since it functions physiologically as provitamin A. In particular, recent scientific findings that β-carotene also acts physiologically as an antioxidant and a radical quencher and moreover has been proven to contribute to cancer prophylaxis (Erdmann, J. W., Grummer, M. A., Does β-Carotene Consumption lower Cancer Risk) Backgrounder Vol. 1, no. 1, Vitamin Nutrition Service, USA, 1984), have led to it becoming of greater interest to a larger group of consumers.

Industry has attempted to respond to the stimulated demand on the one hand by synthethic production of β-carotene and on the other hand by extracting and subsequently crystallizing β-carotene from natural sources. The consumers in accordance with their present critical attitude towards synthetic products have a clear preference for natural β-carotene.

Whereas until recently only the "classical" natural β-carotene sources such as e.g. carrots or algae were available for commercial isolation processes, innovative biotechnological approaches have nowadays exploited a considerably more suitable profound source using fermentative methods. The fermentation of particular filamentous fungi has enabled a concentration of up to more than 5 % by weight β-carotene to be achieved in the dried fermentation biomass; the concentration of β-carotene is therefore about ten higher than in the traditional natural sources. Also, especially due to the new biotechnological developments, industry is considerably interested in extraction procedures which enables the natural β-carotene to be extracted in an economic manner from the complex matrix of the natural materials. Numerous processes are already known for the extraction of β-carotene from solid natural materials. As described for example in the U.S. Pat. No. 2,170,872 the biological matrix is often treated with alkali in order to achieve a cell lysis and saponification of the glycerides. Subsequently the lysed cells are extracted with petroleum ether, heptane or similar solvents. The extract, freed of fibrous materials, is subjected to steam distillation. Subsequently the aqueous residue is extracted with vegetable oil in which β-carotene has a relatively high solubility.

According to a process which is described in the German unexamined laid-open patent application DE 43 42 798, carotinoids can be extracted directly from algae from a highly concentrated salt brine culture using large amounts of edible oil by promoting the mass transfer by means of a colloid mill. The carotene can be enriched by recirculating the oil loaded with extract, the obtained product either being the oil containing β-carotene or the β-carotene must first be precipitated from the oil by crystallization. However, experience shows that the crystallization of β-carotene from oil utilizing temperature-dependent differences in solubility is not without problems since the formation of crystals is very slow and the oil still contains relatively high amounts of residual β-carotene even at low temperatures so that only low crystallization yields are achieved.

In contrast, the induction of β-carotene crystallization by adding solvents invariably leads to higher yields, however, it is necessary to add large amounts of solvent as described for n-propanol for example in the U.S. Pat. No. 1,988,031 in order to obtain a satisfying yield. When extracting from natural materials using organic solvents such as e.g. petroleum ether (cf. the U.S. Pat. Nos. 1,967,121 and 1,998,031) there is generally the problem that, due to the low solubility of β-carotene, and in particular in the case of high β-carotene concentrations, an extremely large amount of solvent must be selected which, however, in turn considerably and negatively effects the space-time yield.

Recently, several processes have been described in which β-carotene is extracted from natural materials using supercritical carbon dioxide at very high process pressures (U.S. Pat. No. 4,400,398). Despite the good extraction results a general disadvantage of this gas extraction process is the complicated technical implementation of the required high pressure which is generally more cost-intensive than processes which operate under normal pressure.

Within the framework of the unification of the food law legislation within the EU, a draft of a guideline to lay down specific purity criteria for dyes which can be used in foods was submitted to the commission in January 1995. In this document the solvents acetone, methyl-ethylketone, methanol, ethanol, propan-2-ol, hexane, dichloromethane and carbon dioxide are proposed for extracting natural carotenes. However, with the exception of dichloromethane, these solvents are less suitable for economic extraction from natural materials in which β-carotene occurs in high concentrations due to their low dissolving capacity for β-carotene. On the other hand a forward-looking food industry should refrain from using dichloromethane for ecological and consumer-related reasons.

The object of the present invention is therefore to provide a process for isolating carotenes, in particular β-carotene, from natural sources and in particular from solid natural materials which is as economical as possible using a liquid extraction agent which circumvents the disadvantages of the known processes. The process should additionally enable a good crystallization yield of β-carotene after the extraction. In particular only those solvents should be used which can be classified as advantageous from an ecological and toxicological point of view.

THE INVENTION

This object is achieved with a process for the extraction of carotenes in which the starting material is extracted at temperatures of at least 30° C. with a solvent mixture which contains acetic acid esters of $C_1$–$C_4$ alcohols and 1 to 25% by weight of an oil related to the acetic acid esters.

Initially, acetic acid esters appear to be less suitable compared to an oil for extracting carotenes since they have a comparatively low dissolving capacity for such compounds. However, it was surprisingly found that they are excellently suitable as extraction agents for carotenes at temperatures higher than 30° C. and in particular at a temperature between 40° C. and 125° C.

The solubility of carotenes initially behaves as expected in a mixture of acetic acid esters on the one hand and oil on the other hand at extraction temperatures <30° C. i.e. directly proportional to the proportion of oil in the solvent mixture i.e. the solubility of the carotenes in the mixture can be determined very simply with a graph by interpolating the solubility in pure ethyl acetate or butyl acetate and oil. However, it was surprisingly found with the process according to the invention that the solubilities of carotenes, in particular of β-carotene, can be increased considerably in acetic acid esters at increased temperatures by the addition of small amounts of oil. This was completely unexpected.

In the process according to the invention the acetic esters of $C_2$–$C_4$ alcohols are preferably used. Particularly preferred acetic esters are ethyl acetate, butyl acetate and mixtures thereof which according to the extraction solvent regulation of 8th Nov. 1991 enclosure 1—meanwhile valid for the whole of Europe—can be used generally in the production of foods.

Oils of biological origin have proven to be particularly suitable according to the invention for the present process. Possible vegetable oils are corn oil, soya oil, cottonseed oil, rape-seed oil and also peanut oil; however, microbial oils from certain fungi, yeasts or bacteria are also suitable like fish oils which can be used for a product in food quality. In special cases it may be of advantage for the present process if the natural oil content in the starting material is adjusted to suitable values by appropriate deoiling measures or by adding oil before starting the extraction.

The addition of oil in an amount of less than 5 % by weight to the solvent mixture can already lead to a substantial increase in the solubility of the colorants. Therefore according to the invention the oil is preferably used in amounts of at least 3 % by weight and particularly preferably between 5 and 10 % by weight in the solvent mixture. Although the solubility of carotenes in the solvent mixture can be further increased by an amount of 10 % and above all 15 % by weight oil, the decisive advantage of the process, namely the high yields of carotenes that can be isolated after the extraction is lost. Although at low concentrations of oil in the mixture the yield can be still increased in the subsequent crystallization of the carotene, a higher amount of oil in the solvent is, however, preferable to achieve the extractive intention.

Temperatures of >50° C. have proven to be particularly suitable for the extraction with the solvent oil mixture since the improvement of the solubility which can be achieved by adding oil is more pronounced at higher temperatures; the upper limit of the process temperature is of course the boiling point of the respective solvent (ethyl acetate: 77° C., butyl acetate: 123°–126° C.) which, however, is generally not reached in the process. In the process according to the invention an especially suitable temperature range for the extraction is thus between 50 and 70° C. 3 to 5 parts by weight of solvent mixture are preferably added per part by weight of solid starting material after which this extraction mixture is usually treated for a period of 1 to 3 hours which is most simply accomplished by stirring. After separation of the solvent mixture is completed for example by centrifugation, the extracted residue is preferably rewashed with 0.5 to 5 parts by weight acetic acid ester e.g. ethyl acetate and/or butyl acetate which can also be carried out several times and the quantities of solvent from the rewashing process are combined with the solvent quantities separated from the oil. The pure carotene is obtained according to known processes by for example by removing the organic solvents in a vacuum or by applying a temperature gradient upon which the carotene accumulates as a crystalline substance.

An important advantage of the new process is that on the one hand a dissolving capacity for carotenes that is comparable to oil can be achieved which considerably improves the space-time yields since overall less solvent is required; on the other hand, since only a small amount of oil is present in the solvent mixture it is possible to achieve a considerably higher yield of crystalline carotene after extraction and removing the solvent mixture since the absolute losses due to the residual solubility of carotene in the small amount of oil are only very small. An important feature of the process of the invention for the extraction of carotenes, especially of β-carotene from natural products, is that the process combines the advantages of a pure oil extraction i.e. the favorable space-time yields due to the high solubility of the carotene colorants especially in the oil and the advantages of pure solvent extraction i.e. the high yields of crystallization.

The following examples are intended to elucidate the advantages of the process according to the invention.

EXAMPLES

In each case one part by weight of a previously defatted and dried fermentation residue of a β-carotene-producing bud-forming fungus (β-carotene content 3.0 % by weight) was stirred vigorously with 4 parts by weight of the solvents or solvent mixtures stated in the following table over a period of 2 hours at the stated process temperatures. Subsequently the biomass was separated over a cloth centrifuge and rewashed with 1 part by weight of the solvent or solvent mixture set to the extraction temperature. After the solvent (mixture) had been removed in a vacuum from the combined carotene-containing extraction solutions, the remaining concentration of β-carotene in the residue after drying was determined and the extraction yield was determined. A corn oil in edible oil quality was used as the oil component.

| Example No. | Solvent or solvent mixture | Process temperature (°C.) | Extraction yield β-carotene (%) |
| --- | --- | --- | --- |
| 1 (ref.) | ethyl acetate | 70 | 66 |
| 2 | ethyl acetate + 6% by weight oil | 70 | >95 |
| 3 | ethyl acetate + 10% by weight oil | 70 | >95 |
| 4 (ref.) | ethyl acetate | 50 | 45 |
| 5 | ethyl acetate + 6% by weight oil | 50 | 80 |
| 6 (ref.) | butyl acetate | 70 | 71 |
| 7 | butyl acetate + 3% by weight oil | 70 | 90 |
| 8 | butyl acetate + 20% by weight oil | 70 | >95 |
| 9 (ref.) | butyl acetate | 50 | 75 |
| 10 | butyl acetate + 10% by weight oil | 50 | 90 |

-continued

| Example No. | Solvent or solvent mixture | Process temperature (°C.) | Extraction yield β-carotene (%) |
|---|---|---|---|
| 11 (ref.) | 30% by weight ethyl acetate + 70% by weight butyl acetate | 70 | 68 |
| 12 | 30% by weight ethyl acetate + 70% by weight butyl acetate + 10% by weight oil | 70 | 90 |

It will be understood that the specification and examples are illustrative but not limitative of the present invention and that other embodiments within the spirit and scope of the inventions will suggest themselves to those skilled in the art.

We claim:

1. A process for the extraction of a carotene from a natural source using a liquid organic extraction agent, comprising: contacting a carotene containing starting material with a solvent mixture consisting essentially of at least one acetic acid ester of $C_1$–$C_4$ alcohols and 1 to 25 % by weight of an oil related to the acetic acid esters at a temperature of at least 30° C.

2. The process of claim 1 wherein the carotene to be extracted is β-carotene.

3. The process of claim 1 wherein the acetic acid ester is selected from ethyl acetate, butyl acetate, and mixtures thereof.

4. The process of claim 1 wherein the oil is of biological origin.

5. The process of claim 1 wherein the oil is used in portions between 5 and 10% by weight in the solvent mixture.

6. The process of claim 1 wherein the extraction is carried out at a temperature between 50° and 70° C.

7. The process of claim 1 wherein 3 to 5 parts by weight solvent mixture are added per part by weight of starting material.

8. The process of claim 1 wherein the extraction mixture is treated for 1 to 3 hours.

9. The process of claim 1 wherein an extraction residue is separated from the mixture and is re-washed with 0.5 to 5 parts by weight acetic acid ester.

* * * * *